United States Patent
Paulson

(10) Patent No.: US 10,369,056 B2
(45) Date of Patent: Aug. 6, 2019

(54) SYSTEM FOR TREATMENT OF EYE CONDITIONS

(71) Applicant: Suzanne Paulson, Temecula, CA (US)

(72) Inventor: Suzanne Paulson, Temecula, CA (US)

( * ) Notice: Subject to any disclaimer, the term of this patent is extended or adjusted under 35 U.S.C. 154(b) by 0 days.

(21) Appl. No.: 16/056,302

(22) Filed: Aug. 6, 2018

(65) Prior Publication Data
US 2018/0338864 A1 Nov. 29, 2018

Related U.S. Application Data

(60) Provisional application No. 62/640,314, filed on Mar. 8, 2018.

(51) Int. Cl.
| | |
|---|---|
| *A61H 33/04* | (2006.01) |
| *A61F 9/04* | (2006.01) |
| *A61F 13/12* | (2006.01) |
| *A61F 7/00* | (2006.01) |
| *A61F 9/00* | (2006.01) |
| *A61F 7/02* | (2006.01) |

(52) U.S. Cl.
CPC ............... *A61F 9/04* (2013.01); *A61F 7/007* (2013.01); *A61F 7/02* (2013.01); *A61F 9/0008* (2013.01); *A61F 13/124* (2013.01); *A61F 2007/0004* (2013.01); *A61F 2007/0078* (2013.01); *A61F 2007/0228* (2013.01); *A61F 2007/0242* (2013.01); *A61F 2007/0277* (2013.01)

(58) Field of Classification Search
CPC .. A61F 9/04; A61F 7/007; A61F 9/008; A61F 13/124; A61F 2007/0004; A61F 2007/0078; A61F 2007/0277
USPC .......................................................... 604/301
See application file for complete search history.

(56) References Cited

U.S. PATENT DOCUMENTS

| | | | | |
|---|---|---|---|---|
| 6,641,264 B1* | 11/2003 | Schwebel | ............... | A42B 1/247 351/158 |
| 2006/0157064 A1* | 7/2006 | Davison | .................. | A61F 9/029 128/858 |
| 2016/0106576 A1* | 4/2016 | Badawi | ................. | A61F 13/124 607/109 |
| 2017/0014300 A1* | 1/2017 | Dippo | ....................... | B32B 5/26 |

* cited by examiner

Primary Examiner — Andrew J Mensh
(74) Attorney, Agent, or Firm — Donn K. Harms

(57) ABSTRACT

A dry eye treatment device and method including a pliable thermal pack engageable upon a first side of a vibration ring is provided. The vibration ring has a second side adapted for positioning on the eyelid of a user to communicate vibration thereto from the vibration ring and heat or cold from a bulging portion of the thermal pack communicating through a central opening of the vibration ring. A cover forming a cavity on the face of the user to house the vibration ring and the thermal pack may also be employed.

7 Claims, 3 Drawing Sheets

SYSTEM FOR TREATMENT OF EYE CONDITIONS

This application claims priority to U.S. Provisional Patent Application Ser. No. 62/640,314 filed on Mar. 8, 2018 which is incorporated herein in its entirety by this reference thereto.

FIELD OF THE INVENTION

The system and method herein is generally related to the treatment of dry eye conditions. More particularly it relates to an eye treatment system configured for communicating vibration and heat concurrently or individually, to the eyelid of a user, in combination with a sealed treatment cavity which may be configured to control the humidity to and around the eyes of the user.

BACKGROUND OF THE INVENTION

Lubrication of the eyes is accomplished in humans by a plurality of meibomian gland openings on the eye lid. The openings communicating with the meibomian gland are conventionally assumed to deposit secretions onto the eyelid during blinking. These secretions are distributed in a film on the open eye when a person blinks and moves their eyelid. For persons where such sections are deposited in a normal fashion, a tear or lipid layer is constantly communicated to the eye surface and prevent dry eye states.

However, in a large portion of the population, such secretions from the openings in the eyelid communicating with the meibomian gland are inadequate. As a consequence, the tear or lipid layer on the surface of the eye is inadequate and normal evaporation of the inadequate layer will cause dry eyes.

Approximately 75% of the estimated 60 million people suffering from such inadequate secretions, suffer from a condition known as Evaporative Dry Eye. This results in a decrease of the tear layer quantity and especially the tear layer quality of the patient. The remainder of dry eye sufferers are categorized as suffering from Aqueous Deficient Dry Eye. This results as a function of the quality and quantity of the actual tear production and communication of such to the eyes.

As a result of such tear quantity and quality issues, people suffering such generally experience constant pain from eye irritation, including a sandy or gritty sensation. This is a significant health problem for sufferers. This is because if left untreated, such dry eye conditions are conventionally known to lead to actual physical scarring or ulceration of the cornea. Further, such can easily lead to a partial or total loss of vision.

While such conditions and their causes are a constant subject for research, there is presently no cure for such dry eye conditions suffered by such patients. However, conventionally there are various treatments which are initiated to alleviate the often debilitating pain and discomfort caused by dry eye conditions. Such treatments include: artificial tear solutions, moisture chamber glasses, and punctal occlusion amongst others.

It is medically known that a conventional cause of such dry eyes is a condition involving a dysfunction of the meibomian gland. This occurs when either the passages to the openings in the eyelid or the meibomian glands themselves are occluded where they are partially or completely blocked. A complete blockage or occlusion will prevent secretions from reaching the surface of the eye, whereas a partial occlusion will severely limit the secretions reaching and lubricating the eye.

The depositing of artificial tears to the cornea primarily increases the comfort of people suffering from dry, irritated eyes. However, when used frequently, such artificial tears can rinse away the natural tears and the oils therein necessary to reestablish a normal tear film. Further, such artificial tears do not address the underlying problem of complete or partial occlusions of the passages to or within the meibomian glands. Frequent use of artificial tears is also expensive.

Another treatment includes the use of moisture chamber glasses or frames. Such moisture chamber glasses are custom-made products designed to alleviate the pain and discomfort caused by dry eye conditions. However, such chamber glasses again do nothing to treat the underlying occlusion problem noted above and must be custom fit by an optician, and can be prohibitively expensive for the average consumer. Further, because of the wide differential in the shape of the faces of patients, without a custom fitting of each patient for such chamber glasses, the comfort as well as humidity seal of the chambers to the faces of users are marginal at best.

The system herein is configurable to provide a sealed chamber around one or both eyes of the user and combines the communication of heat from a thermal pack or gel pack in combination with vibration from a ring operatively positioned to contact the eyelids on one side, and the thermal pack or gel pack on an opposing side. The combination of heat from a thermal pack and vibrational therapies is especially well adapted to help clear partial or total blockages within the passage of or to the meibomian glands over time.

It should be noted, the forgoing examples of related art and limitations related therewith are intended to be illustrative and not exclusive, and they do not imply any limitations on the exercise device and method described and claimed herein. Various limitations of the related art are already known or will become apparent to those skilled in the art upon a reading and understanding of the specification below and the accompanying drawings

SUMMARY OF THE INVENTION

The present invention is directed towards a device and method for treating dry eyes and/or irritated eye conditions of a user. Such conditions are caused by an inadequate supply of tears and lubricating oils and agents therein communicated to the surface of the eye from the meibomian glands. The device herein employs a mask or the like which is configured for comfortable facial engagement to an as-used positioning. In this as-used positioning the mask is held against the face surrounding the eye or eyes of the user, to form a treatment cavity adjacent one or both eyes of the user.

So positioned, the device is configurable to maintain a higher level of humidity to one or both eyes of the user then the humidity existing outside the sealed chamber. Further, the device is employable to maintain and/or increase the temperature and humidity around and to the eyes through the inclusion and employment of a thermal pack. Still further the device so configured and situated on the user, aids in limiting evaporation of natural and/or artificial tears.

Additionally provided and particularly preferred, for use in combination with the thermal pack or gel pack, a vibration insert or ring is provided, which is adapted to contact the eyelid on a first surface, and to contact the thermal pack on an opposing surface. The vibrating insert thereby communicates a vibration to both the eye and the thermal pack which contacts the eye of the user within a centrally located aperture. This thermal pack and vibrational ring combination, can be employed on one eye or both eyes and can be employed without the mask or cavity in one mode, but is preferably provided within the cavity of a mask where a humidity increase is desired for communication to the eye or eyes being treated.

In use, the device herein provides a device and method for promoting healthy eyes during use. Such is provided by aiding in thickening the lipid layer on the cornea as well as helping dislodge blockages within the meibomian glands or passages therefrom leading to the interior of the eyelids. As noted, to that end the system may be employed with only the thermal pack and a vibrating ring sandwiched between the thermal pack and an eyelid in a mode where the thermal pack provides the weight to maintain eye contact. Alternatively and preferred, the system may also be employed with a mask surrounding one or both eyes in combination with the thermal pack contacting and covering the eye and a vibrating ring sandwiched therebetween. The system may also be employed for controlled application of medicine to the eyes, and while primarily taught as a heated thermal pack, such can also be employed with a chilled thermal pack to thereby communicate either heat or cold temperature to one or both eyes as needed.

In use, the system herein provides for the communication to the eyes of the user, heat and vibration alone, or when housed in a mask, moist heat in combination with vibration, which experimentation and studies have shown is more therapeutic than dry heat. Moist heat, in experimentation, has been shown to penetrate more deeply, which promotes circulation and hydrates the sensitive eye lid and surrounding skin.

The duration of communication of heat and vibration and/or moist heat and vibration, or in some cases vibration and cold to the eye or eyes treated with the device herein, as well as the actual area of the face covered and treated, is significantly enhanced over the prior art devices and methods.

In a mode where the thermal pack and vibrating ring are combined and positioned withing a pliable flexible mask, a treatment chamber is formed to cover one or both eyes of the patient and the areas surrounding the eye or eyes. In this mode the mask may be configured to cover one or to cover both eyes, and is preferably formed of a flexible polymeric material which has a front wall transitioning to a sidewall portion which forms or has a sealing edge about the perimeter of the sidewall portion.

While the thermal pack and vibrating ring are configured to hold in biased contact against the eyelid through the weight of the thermal pack, when used with a mask surrounding either one or both eyes, it is adapted for engagement using the biasing force of a strap to hold a sealing edge of the mask in sealed engagement to the face of a user.

In the combination using a mask with the thermal pack and vibrating ring, a treatment chamber covering one or both eyes, is formed by the sealed engagement of the sealing edge of the mask with the face of the user. In addition to the temperature altering thermal pack and vibrating ring, the treatment chamber can incorporate a woven or non-woven fabric cover to insulate the temperature differential from the eyes and to provide moisture to the cavity.

The system herein may be employed with a thermal pack or gel pack sized to cover one eye, or a large gel pack configured to contact and cover the eyelids of both eyes. Preferably, a single thermal or gel pack having temperature-storing gel beads or gel, or other pliable temperature storing media, within the confines of a plastic envelope is employed.

The thermal packs or gel packs are pliable and have a pliable media within a cover. A fabric cover may be slid upon the thermal packs and the media within and the pack itself can easily be heated in a microwave, hot water, conventional oven, or cabinet (used in spas to heat towels) using steam. Additionally, the thermal packs can be cooled in ice, freezer, ice water, and refrigerator to provide cooling temperature communication to the eyes within the chamber.

It is an object of this invention to provide a device and system for treatment of dry eye conditions and irritated eyes which communicates a biased temperature altering component against the eyelid concurrently with vibration from a vibrating component such as a transducer or other component which vibrates when electric power is communicated thereto.

Still another object of this invention is to provide such a device which can be employed to help remove or cause expulsion of blockages in ducts or conduit from or in the meibomian glands to treat dry eye conditions caused thereby.

The invention, accordingly, comprises the features of construction, combination of elements, and arrangement of parts which will be exemplified by the constructions hereinafter set forth, and the scope of the invention will be indicated in the claims.

With respect to the above summary description, before explaining at least one preferred embodiment of the herein disclosed eye treatment system in detail, it is to be understood that the invention is not limited in its application to the details of construction and to the arrangement in the following description or illustrated in the drawings. The eye treatment system and method herein described, is capable of other embodiments and of being practiced and carried out in various ways which will become obvious to those skilled in the art on reading this disclosure. Also, it is to be understood that the phraseology and terminology employed herein are for the purpose of description and should not be regarded as limiting.

As such, those skilled in the art will appreciate that the conception upon which this disclosure is based, may readily be utilized as a basis for designing of other vibrating thermal or gel pack combinations and eye engageable treatment systems and devices and for carrying out the several purposes of the present disclosed system. It is important, therefore, that the claims herein be regarded, as including such equivalent construction and methodology, insofar as they do not depart from the spirit and scope of the present invention.

BRIEF DESCRIPTION OF DRAWING FIGURES

The accompanying drawings, which are incorporated herein and form a part of the specification, illustrate some, but not the only or exclusive examples of embodiments and/or features of the invention. It is intended that the embodiments and figures disclosed herein are to be considered illustrative rather than limiting.

DETAILED DESCRIPTION OF THE EXEMPLARY EMBODIMENTS

Figure 1:
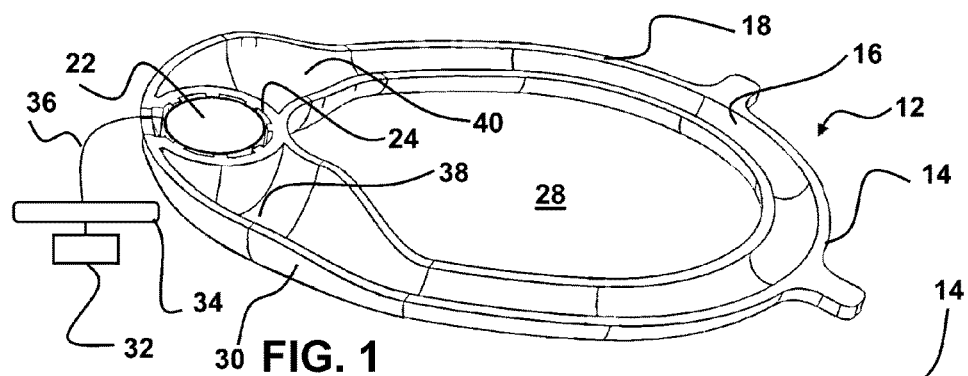
FIG. 1 depicts a perspective view of the vibrating ring of the device herein showing the body thereof having a recess or channel and showing the operative connection of the transducer to a power supply such as a battery and a controller.

In this description, any directional prepositions if employed, such as up, upwardly, down, downwardly, front, back, first, second, top, upper, bottom, lower, left, right and other such terms refer to the device or depictions as such may be oriented are describing such as it appears in the drawings and are used for convenience only. Such terms of direction and location are not intended to be limiting or to imply that the device herein has to be used or positioned in any particular orientation.

Further, while the vibrating component is referred to for convenience as a vibrating member or ring which surrounds and forms a bulging portion of a thermal pack, and such a ring shape is preferred, other configurations of the vibrating ring may be employed which may not form a complete ring or aperture, so long as they include an aperture or the like to form a bulge area in the thermal pack. This bulge area has been found to provide better contact against eyelids, and the ring or a form substantially in a ring shape, has been found to better communicate vibration directly to they eye, and concurrently through the bulge portion of the thermal pack. Further, the ring and central opening have been found to stay positioned better upon an eyelid of a user by encircling around the hemispheric shape in such an engagement. Thus a vibrating component which forms a centrally located bulge positioned to contact the eyelid, is preferred for both temperature communication to the eye and vibration communication to the eye.

Now referring to drawings in FIGS. 1-8, wherein similar components are identified by like reference numerals, there is seen in FIG. 1, a perspective view of the vibration member 12 of the device 10 herein. The vibration member 12 has a body 14 which is formed with a recess 16 depending into a first side 18 of the body 14 thereof.

While the vibration member 12 will function without the recess 16 formed into the first side 18, such is preferred as noted below because experimentation has found that a portion of the soft and pliable thermal pack 20 will settle into the recess 16 and form an enhanced engagement of the thermal pack 20 to the vibration member 12 which has been found to prevent sliding when the user tilts their head. This enhanced engagement of the portion of the thermal pack 20 in experimentation, was also found to enhance the communication of vibration generated by a vibrating component such as a transducer 22, engaged to the vibration member 12 in the opening 24 of the body 14, into the bulge 26 and to the user eye. By vibrating component is meant any component which vibrates upon the communication of electric power thereto such as the depicted transducer 22.

Thus, inclusion of the recess 16 which allows for increased contact area of the thermal pack 20 with the vibration member 12, and thereby enhanced communication of the vibration to the eyelid of the user from a bulge 26 (FIG. 4) formed within in a central opening 28 defined within in the body 14 is especially preferred. As noted, this central opening 28 need not be within a vibration member 12 formed as a ring, but can be a vibration member 12 formed substantially to a ring. By substantially to a ring is meant, that the vibration member 12 surrounds the central opening 28 on at least 80 percent of the circumference of the central opening 28 and thus a small gap (not shown) might be included in a small area. However a complete ring formation of the vibration member 12 is preferred due to increased communication of vibration and strength.

Figure 4:
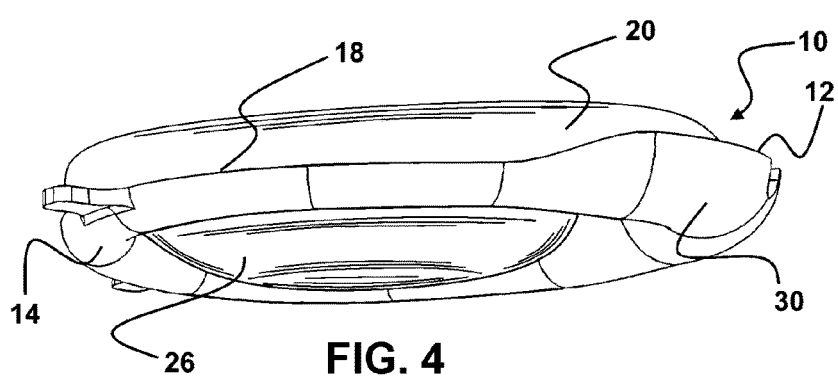
FIG. 4 shows one mode of the device herein as used where the vibration member has the recess thereof operatively engaged with portions of the thermal pack therein and an aperture of the vibrating ring forming a bulge portion of the thermal pack which is placed in contact with the eyelid of a user.

Additionally, the recess 16 proved to form a significantly better engagement between a thermal pack 20 situated against the first side 18 of the body 14 such as shown in FIG. 4, which as shown is the simplest mode of the device 10 herein. With a second side 30 of the device in contact with the eyelid or surrounding facial area of a user in an as-used position of the device 10, the bulge 26 is formed by a portion of the thermal pack 20 from the weight of the thermal pack 20 against the first side 18 of the body 14 of the vibration member 12.

Further, portions of the thermal pack 20 also conform into and engage the recess 16 such that if the user tilts their head, the device 10 stays in an as-used position and the thermal pack 20 stays engaged and does not fall off its engagement against the first side 18 of the body 14. As such, due to the enhanced vibration transmission noted, and the enhance engagement and stability of the thermal pack 20 cooperatively positioned within the recess 16, the inclusion of the recess on the first side 18 of the body 14 of the vibration member is preferred.

As noted the transducer 22 is located in an opening 24 sized for frictional engagement therein. In the mode depicted in FIG. 1, the battery 32 and a controller 34 if employed, are shown remotely positioned and connected to the transducer 22 by a cable 36. However, the battery 32 and a controller 34 can also be engaged to or within the body 14 of the vibration member 12 and in a wired 36 connection to the transducer 22.

It would be preferred to position them to maintain a balance to the mass or weight of the body 14 to maintain stability when the body 14 is engaged with a thermal pack 20 such as in FIG. 4, and the second side 30 and bulge 26 contact the eyelid of the user. Currently, the diameter of the widest point of the recess 16 is between 0.125 and 0.225 inches and such has shown to provide an easily engaged recess 16 for the pliable portions of the thermal pack 20 to settle into and increase contact thereof with the vibration member 12.

Figure 2:
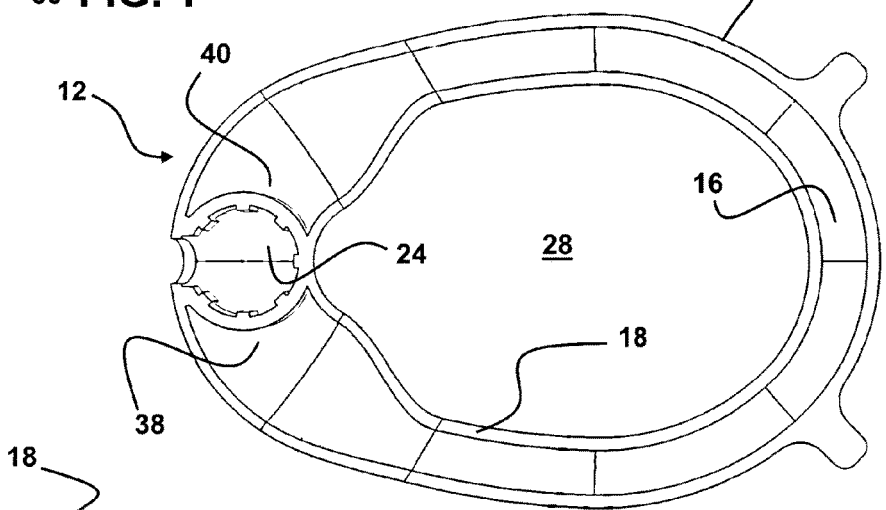
FIG. 2 is an overhead plan view of the vibration member or vibrating ring of FIG. 1 showing the preferred configuration of the body having a channel communicating around an oval or circular pathway to both sides of a recess housing the transducer.

Further, as shown in FIGS. 1-2, the recess 16 is formed in a complete oval or circular shape within the body 14 of the vibration member 12. This is preferred as it has been found having a first end 38 of the recess 16 and the second end 40 of the recess 16 both in contact or communication with opposing sides of the transducer 22, with an uninterrupted recess 16 running therebetween, enhances the communication of vibrations generated by the transducer 22 into the recess 16 and/or the portion of the thermal pack 20 which settles therein such as shown in FIG. 4.

The body 14 of the vibration member may be formed of metal or polymeric materials or of metal coated with a softer polymeric material. Currently, the body is formed of a polymeric material such as rubbers/elastomers, plastics such as polyolefins, fluoropolymers, vinyls, polypropylene, polyethylene, poly styrene, and any other polymeric material adapted to the task as would occur to those skilled in the art. Such polymeric materials have been better received by patients in experimentation as it provides a softer contact against the eyelid and/or skin surrounding the eye. When formed of a polymeric material such currently has a preferred shore hardness in a range of hardness between 35 A to 70 D with a hardness between 55 A to 65 A being especially preferred.

As noted, FIG. 2 shows an overhead plan view of the vibration ring 12 depicted in the various figures herein. As can be seen the recess 16 is formed in a ring or loop communicating around an oval or circular pathway depending into the first side 18 of the body 14. This forms an oval or circular track out of the recess 16 with the first end 38 and second end 40 thereof adjacent the transducer 22.

As noted and shown in FIGS. 1-4 for example, an opening 28 is formed in a central portion of the body 14, which is surrounded and adjacent to the portion of the body 14 defining the recess 16. The opening 28 is particularly preferred as it provides sufficient rigidity to cause the thermal pack 20 positioned against the first side 18 of the body 14, to form a bulge 26 which communicates through the opening 28. This bulge 26 will generally project through the opening in a self-regulating distance once the bulge 26 contacts the eyelid of the user with the device situated for example, in the configuration of FIG. 4. It has been found that forming the opening 28 with a perimeter which is round or substantially oval, provides the best rigid structure to support and form the bulge 26 and form an engaged thermal pack 20.

Figure 3:
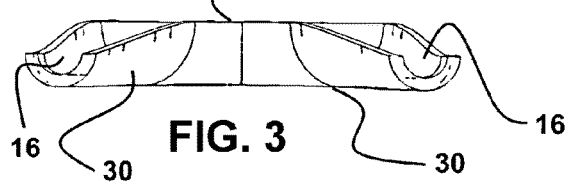
FIG. 3 is a sectional view along line 3-3 of FIG. 2 showing the recess in the vibration member and the depth and width thereof.

Shown in FIG. 3 as noted, is a sectional view of FIG. 2. As can be seen, the recess 16 communicates from both the first and second end thereof. Currently, a depth of the recess 16 below the first side 18 of the body 14 of the vibrating member 12 of 0.15 to 0.30 inches is preferred. Such allows the pliable material of the thermal pack 20 to settle into the recess 16 a sufficient distance to maintain an engagement if the user tilts their head when lying on their back with the device 10 contacting one or both eyes.

Depicted in FIG. 4, is a mode of the device 10 herein which, as noted, would be positioned to the as-used position in operative contact with one eye of a user. As shown, the vibration member 12 has the recess 16 therein operatively engaged with portions of the thermal pack 20. The opening 24 in the body 14 of the vibration member 12 constricts a central portion of the thermal pack 20 such that a bulge 26 portion is formed in the thermal pack 20. Bulge 26 contacts the eyelid of the user and communicates heat to the eyelid concurrently with vibrations generated by the transducer 22 and communicated through the material in the thermal pack 20. Additionally, the second side 30 of the body 14 of the vibration member 12 also provides a vibrating contact surface against the eyelid or tissue surrounding the eye or eyelid of the user.

Figure 5:
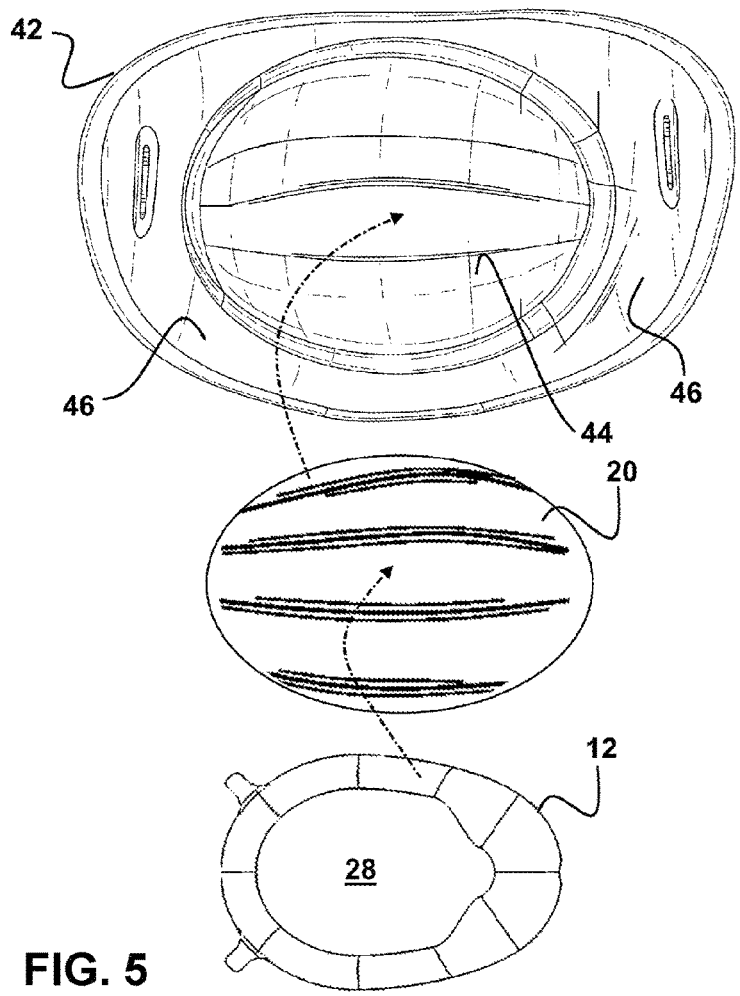
FIG. 5 depicts a mode of the device herein, wherein the device as shown in FIG. 4 is positioned within a cavity of a cover configured to sealably engage around one eye.

Shown in FIG. 5 is shown an exploded view of another mode of the device herein additionally including a cover 42 used in combination with the thermal pack 20 and vibration member 12 in contact therewith. The cover 42 has a defined cavity 44 therein surrounded on a perimeter of the cavity 44 by a sealing edge 46. The shown components are assembled to the configuration shown in FIG. 6. In use a moisture source such as a fabric cover (not shown) for the thermal pack 20 can be included to induce a higher humidity level in the cavity 44 than the air or atmosphere outside the cavity 44 which is in sealed engagement against the skin of the user with the sealing edge 46. A strap may be employed to bias the sealing edge 46 against the skin to maintain a seal.

Figure 6:
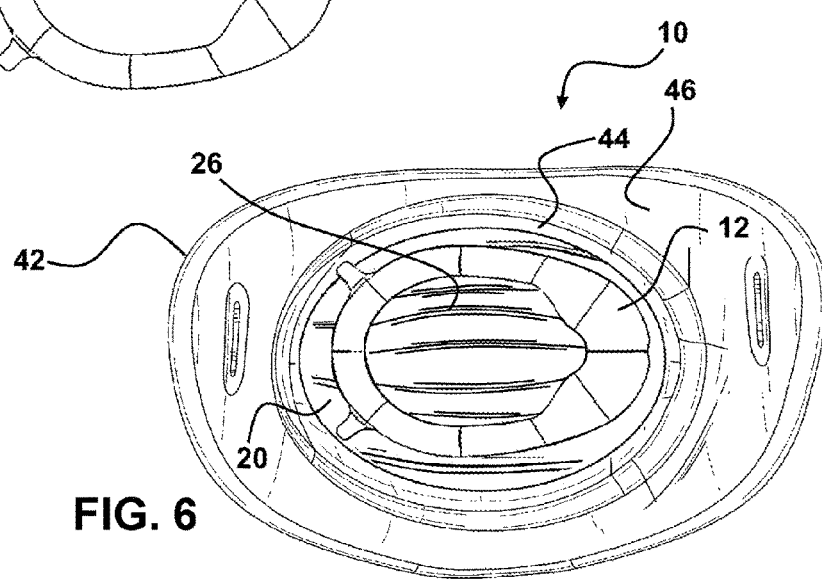
FIG. 6 shows the device in the exploded view of FIG. 5, operatively positioned for as-used positioning against and around one eye of a user.
Figure 7:
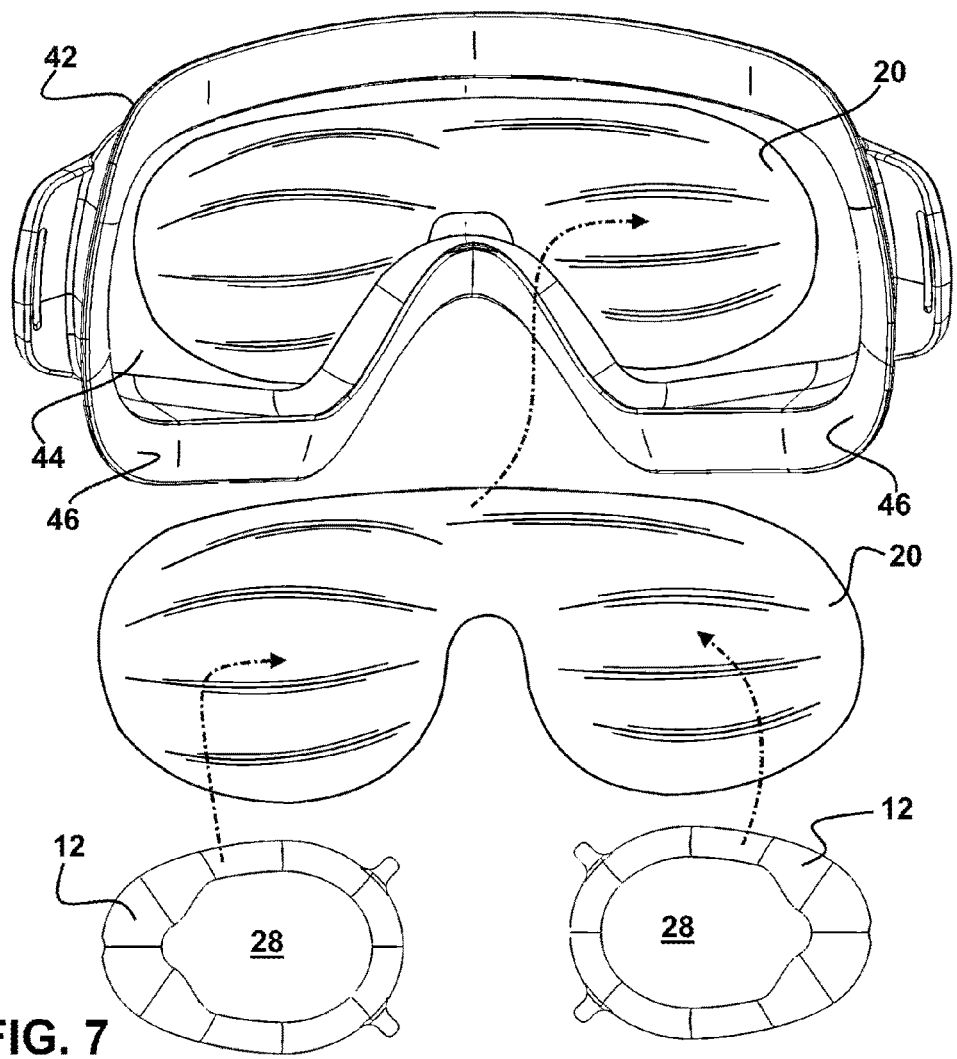
FIG. 7 depicts an exploded view of a mode of the device herein, wherein the device in a similar fashion as shown in FIG. 4 is positioned with two vibration members contacting portions of a thermal pack, which are operatively located within a cavity of a cover configured to sealably engage around both eyes.

Depicted in FIG. 7 is shown an exploded view of another mode of the device herein, similar to that of FIG. 5-6, but with a cover 42 having a cavity 44 to seal around both eyes of the user. The cover 42 with such a cavity 44 is employed in combination with the thermal pack 20 and vibration member 12 in contact therewith. The cover 42 has the defined cavity 44 therein surrounded by a sealing edge 46 which forms a sealed engagement with the face around both eyes of a user.

Figure 8:
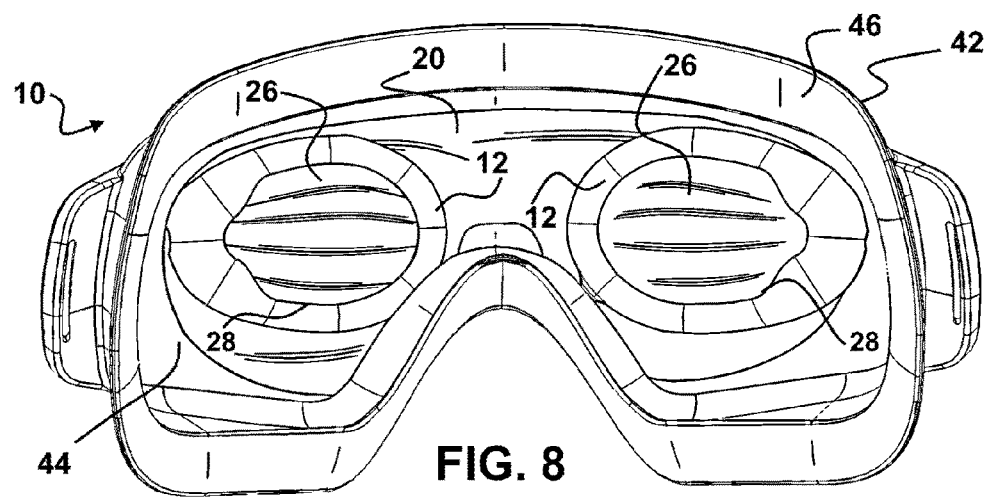
FIG. 8 shows the device in the exploded view of FIG. 7, with the noted components operatively positioned for as-used positioning with the two vibration members and bulging gel pack portions located therein in contact against and around both eyes of a user.

The shown components of FIG. 7 are assembled to the configuration shown in FIG. 8. As with the single eye mode of FIGS. 5-6, in use a moisture source such as a moistened fabric cover (not shown) for the thermal pack 20, can be included to induce a higher humidity level in air within the cavity 44 than that of the air or atmosphere outside the cavity 44, when the sealing edge 46 is in the sealed engagement against the skin of the user. As noted, an elastic or cinchable strap which is well known to those skilled in the art and need not be shown, may be employed to bias the sealing edge 46 against the skin to maintain a seal.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications as would occur to those skilled in the art are considered to be within the scope of this invention as broadly defined in the appended claims.

Further, the purpose of the attached abstract is to enable the U.S. Patent and Trademark Office and the public generally, especially scientists, engineers and practitioners in the art who are not familiar with patent or legal terms or phraseology to determine quickly, from a cursory inspection, the nature and essence of the technical disclosure of the application. The abstract is neither intended to define the invention of the application, which is measured by the claims, nor is it intended to be limiting as to the scope of the invention in any way.

What is claimed is:

1. A dry eye treatment apparatus comprising:
   a pliable thermal pack, said thermal pack having media therein adapted to store heat or cold communicated thereto;
   a vibration ring having a substantially ring shaped body surrounding a central opening within said vibration ring;
   a vibration component engaged to said vibration ring, said vibration component communicating vibration to said vibration ring upon communication of electric power thereto;
   said vibration ring having a first side;
   said vibration ring having a second side configured for positioning upon an eyelid of a user;
   said thermal pack having an engaged position in contact with said first side of said vibration ring;
   a recess depending into said first side of said body of said vibration ring;
   said recess forming an increased contact area for contact of a portion of said thermal pack positioned therein to said engaged position;
   said increased contact area of said portion of said thermal pack within said recess, stabilizing said thermal pack in said engaged position and preventing sliding upon said first side of said body;
   said increase area of contact area of said portion of said thermal pack within said recess providing an increase in said vibration from said vibration ring communicated to said bulging portion of said thermal pack;
   said thermal pack in said engaged position having a bulging portion thereof projecting through said central opening and projecting past said second side, whereby said vibrating ring is positionable with said thermal pack in said contact with said first side of said body and said second side in contact with said eyelid of a user to thereby position said bulging portion in contact with said eyelid to concurrently communicate said vibration from said vibration ring and said heat or cold from said media in said thermal pack, to said eyelid.

2. The dry eye treatment apparatus of claim 1, additionally comprising:
   said recess extending from a first end of said recess adjacent a first side of a mounting area on said body for said vibration component, to a second end of said recess, said second end of said recess located on a second side of said mounting area from said first side of said recess.

3. The dry eye treatment apparatus of claim 1, additionally comprising:
   a cover, said cover having a sealing edge adapted to seal against the face of a user surrounding an eye of said user when placed in an operative position;
   said sealing edge defining a cavity of said cover;
   said vibration ring positioned within said cavity with said thermal pack in said engaged position thereon; and
   whereby said vibrating ring is positionable with said second side of said body thereof in said contact with said eyelid and said bulging portion in contact with said eyelid to thereby concurrently communicate said vibration from said vibration ring and said heat or cold from said media in said thermal pack, to said eyelid within said cavity.

4. The dry eye treatment apparatus of claim 2, additionally comprising:
   a cover, said cover having a sealing edge adapted to seal against the face of a user surrounding an eye of said user when placed in an operative position;
   said sealing edge defining a cavity of said cover;
   said vibration ring positioned within said cavity with said thermal pack in said engaged position thereon; and
   whereby said vibrating ring is positionable with said second side of said body thereof in said contact with said eyelid and said bulging portion in contact with said eyelid to thereby concurrently communicate said vibration from said vibration ring and said heat or cold from said media in said thermal pack, to said eyelid within said cavity.

5. The dry eye treatment apparatus of claim 3, additionally comprising:
   said cover having a sealing edge adapted to seal against the face of a user with said sealing edge surrounding both of two eyes of said user when placed in an operative position sealed against said face of said user;
   said sealing edge defining said cavity of said cover adapted to surround both of said two eyes of said user during placement in said operative position;
   a pair of said vibration rings positioned within said cavity, each of said pair having a said thermal pack in said engaged position thereon; and
   whereby said pair of vibrating rings are positionable with a respective said second side of each one of said pair of vibrating rings, in a respective said contact with one of a pair of eyelids of said user, and with a respective said bulging portion in each of said pair of vibrating rings in contact with a respective one of said eyelids, to thereby concurrently communicate said vibration from a said vibration ring and said heat or cold from said media in said thermal pack, to both respective said eyelids within said cavity.

6. The dry eye treatment apparatus of claim 4, additionally comprising:
   said cover having a sealing edge adapted to seal against the face of a user with said sealing edge surrounding both of two eyes of said user when placed in an operative position sealed against said face of said user;
   said sealing edge defining said cavity of said cover adapted to surround both of said two eyes of said user during placement in said operative position;
   a pair of said vibration rings positioned within said cavity, each of said pair having a said thermal pack in said engaged position thereon; and
   whereby said pair of vibrating rings are positionable with a respective said second side of each one of said pair of vibrating rings, in a respective said contact with one of a pair of eyelids of said user, and with a respective said bulging portion in each of said pair of vibrating rings in contact with a respective one of said eyelids, to thereby concurrently communicate said vibration from a said vibration ring and said heat or cold from said media in said thermal pack, to both respective said eyelids within said cavity.

7. A method of employment of the dry eye treatment apparatus of claim 1 comprising:
   placing said second side of said vibration ring upon an eyelid of a user;
   positioning said thermal pack to said engaged position supported upon said first side of said vibration ring;
   positioning said portion of said thermal pack within said recess; and
   activating said vibration component engaged to said vibration ring, to thereby communicate vibration to said thermal pack supported by said first side of said vibration ring and to said bulging portion of said thermal pack by communicating electric power to said vibration component.

* * * * *